(12) United States Patent
Itsenko et al.

(10) Patent No.: US 7,553,942 B2
(45) Date of Patent: *Jun. 30, 2009

(54) METHOD FOR THE USE OF [$^{11}$C] CARBON MONOXIDE IN LABELING SYNTHESIS OF $^{11}$C-LABELLED AMIDES USING METAL AMIDES AND PHOTO-INDUCED FREE RADICAL CARBONYLATION

(75) Inventors: Oleksiy Itsenko, Uppsala (SE); Tor Kihlberg, Uppsala (SE); Bengt Langstrom, Uppsala (SE)

(73) Assignee: GE Healthcare Limited, Buckinghamshire (GB)

( * ) Notice: Subject to any disclaimer, the term of this patent is extended or adjusted under 35 U.S.C. 154(b) by 187 days.

This patent is subject to a terminal disclaimer.

(21) Appl. No.: 11/268,107

(22) Filed: Nov. 7, 2005

(65) Prior Publication Data

US 2006/0133998 A1 Jun. 22, 2006

Related U.S. Application Data

(60) Provisional application No. 60/625,377, filed on Nov. 5, 2004.

(51) Int. Cl.
*C07F 5/00* (2006.01)
*C07C 233/02* (2006.01)
*B01J 19/08* (2006.01)

(52) U.S. Cl. .......................... 534/11; 204/89; 204/157; 422/159; 422/186; 564/123

(58) Field of Classification Search ................. 554/111; 204/157.89, 89, 157; 422/159, 186; 564/123; 534/11
See application file for complete search history.

(56) References Cited

FOREIGN PATENT DOCUMENTS

WO WO 02/102711 A1 * 12/2002

OTHER PUBLICATIONS

Obaidur Rahman, Tor Kihlberg, and Bengt Langstrom Aryl Triflates and [11 C]/(13C) Carbon Monoxide in the Synthesis of 11C-/13C-Amides J.Org. Chem. 2003, 68, 3558-3562.*

Itsenko, Oleksiy, et.al. "Photoinitiated Carbonylation with [11C] Carbon Monoxide Using Amines and Alkyl Iodides" Journal of Organic Chemistry, vol. 69, No. 13, 2004, pp. 4356-4360.

Ryu, I. et.al. "Metal Catalyst-Free by Design. The synthesis of amides from alkyl iodides carbon monoxide and amines by a hybrid radical/ionic reaction" Chemical Communications-Chemcom, royal society of Chemistry, GB, 1998, pp. 1953-1954.

Ryu, I "Radical carbonylation of iodoalkanes and saturated alcohols using carbon monoxide" Chem. Soc. Rev., vol. 30, 2001, pp. 16-25.

Rahman O, et.al., Aryl Triflates and 11C/13C Carbon Monoxide in the Synthesis of 11C/13C amides Journal of Organic Chemistry, American Chemical Society, Easton, US, vol. 68, May 9, 2003, pp. 3558-3562.

Kihlberg, T. et.al. "Biologically Active C-labeled amides using palladium-mediated reactions with aryl halides and 11C Carbon Monoxide" Journal of Organic Chemistry, American Cehmical Society Easton US, vol. 64, 1999, pp. 9201-9205.

F. Karimi, et.al., "Synthesis of 11C-labelled amides by palladium-mediated carboxamination using [11C]Carbon monoxide, in situ activated amines and 1,2,2,6,6-Pentapiperidine" European Journal of Organic Chemistry, 2003, pp. 2132-2137.

F. Karimi, et.al., "Synthesis of 11C-amides using [11C]-carbon monoxide and in situ activiated amines by palladium-mediated carboxaminations" Or. Biomol. Chem. vol. 1, 2003, pp. 541-546.

Sergio Kreimerman, et.al. "Synthesis of nitrogen heterocycles based on atom transfer carbonylation of bifunctional amines" C.R. Acad. Sci. Paris, Chimie/Chemistry, vol. 4, 2001, pp. 497-503.

Int'l Search Report and written opinion PCT/IB2005/004086 dated Jun. 2006.

* cited by examiner

*Primary Examiner*—Shailendra Kumar
(74) *Attorney, Agent, or Firm*—Craig Bohlken

(57) ABSTRACT

Methods and reagents for photo-initiated carbonylation with carbon-isotope labeled carbon monoxide using weakly nucleophilic amines and alkyl/aryl iodides are provided. The resultant carbon-isotope labeled amides are useful as radiopharmaceuticals, especially for use in Positron Emission Tomography (PET). Associated kits for PET studies are also provided.

11 Claims, 7 Drawing Sheets

METHOD FOR THE USE OF [¹¹C] CARBON MONOXIDE IN LABELING SYNTHESIS OF ¹¹C-LABELLED AMIDES USING METAL AMIDES AND PHOTO-INDUCED FREE RADICAL CARBONYLATION

This application claims benefit of 60/625,377, filed Nov. 5, 2004.

FIELD OF THE INVENTION

The present invention relates to a method and an apparatus for the use of carbon-isotope monoxide in labeling synthesis. More specifically, the invention relates to a method and apparatus for producing an [$^{11}$C]carbon monoxide enriched gas mixture from an initial [$^{11}$C]carbon dioxide gas mixture, and using the produced gas mixture in labeling synthesis by photo-initiated carbonylation. Radiolabeled amides are provided using amines treated with alkali metal base and alkyl iodides as precursors.

BACKGROUND OF THE INVENTION

Tracers labeled with short-lived positron emitting radionuclides (e.g. $^{11}$C, $t_{1/2}$=20.3 min) are frequently used in various non-invasive in vivo studies in combination with positron emission tomography (PET). Because of the radioactivity, the short half-lives and the submicromolar amounts of the labeled substances, extraordinary synthetic procedures are required for the production of these tracers. An important part of the elaboration of these procedures is development and handling of new $^{11}$C-labelled precursors. This is important not only for labeling new types of compounds, but also for increasing the possibility of labeling a given compound in different positions.

During the last two decades carbonylation chemistry using carbon monoxide has developed significantly. The recent development of methods such as palladium-catalysed carbonylative coupling reactions has provided a mild and efficient tool for the transformation of carbon monoxide into different carbonyl compounds.

Carbonylation reactions using [$^{11}$C]carbon monoxide has a primary value for PET-tracer synthesis since biologically active substances often contain carbonyl groups or functionalities that can be derived from a carbonyl group. The syntheses are tolerant to most functional groups, which means that complex building blocks can be assembled in the carbonylation step to yield the target compound. This is particularly valuable in PET-tracer synthesis where the unlabelled substrates should be combined with the labeled precursor as late as possible in the reaction sequence, in order to decrease synthesis-time and thus optimize the uncorrected radiochemical yield.

When compounds are labeled with $^{11}$C, it is usually important to maximize specific radioactivity. In order to achieve this, the isotopic dilution and the synthesis time must be minimized. Isotopic dilution from atmospheric carbon dioxide may be substantial when [$^{11}$C]carbon dioxide is used in a labeling reaction. Due to the low reactivity and atmospheric concentration of carbon monoxide (0.1 ppm vs. 3.4×10$^4$ ppm for CO$_2$), this problem is reduced with reactions using [$^{11}$C] carbon monoxide.

The synthesis of [$^{11}$C]carbon monoxide from [$^{11}$C]carbon dioxide using a heated column containing reducing agents such as zinc, charcoal or molybdenum has been described previously in several publications. Although [$^{11}$C]carbon monoxide was one of the first $^{11}$C-labelled compounds to be applied in tracer experiments in human, it has until recently not found any practical use in the production of PET-tracers. One reason for this is the low solubility and relative slow reaction rate of [$^{11}$C]carbon monoxide which causes low trapping efficiency in reaction media. The general procedure using precursors such as [$^{11}$C]methyl iodide, [$^{11}$C]hydrogen cyanide or [$^{11}$C]carbon dioxide is to transfer the radioactivity in a gas-phase, and trap the radioactivity by leading the gas stream through a reaction medium. Until recently this has been the only accessible procedure to handle [$^{11}$C]carbon monoxide in labeling synthesis. With this approach, the main part of the labeling syntheses with [$^{11}$C]carbon monoxide can be expected to give a very low yield or fail completely.

There are only a few examples of practically valuable $^{11}$C-labelling syntheses using high pressure techniques (>300 bar). In principal, high pressures can be utilized for increasing reaction rates and minimizing the amounts of reagents. One problem with this approach is how to confine the labeled precursor in a small high-pressure reactor. Another problem is the construction of the reactor. If a common column type of reactor is used (i.e. a cylinder with tubing attached to each end), the gas-phase will actually become efficiently excluded from the liquid phase at pressurization. The reason is that the gas-phase, in contracted form, will escape into the attached tubing and away from the bulk amount of the liquid reagent.

The cold-trap technique is widely used in the handling of $^{11}$C-labelled precursors, particularly in the case of [$^{11}$C]carbon dioxide. The procedure has, however, only been performed in one single step and the labeled compound was always released in a continuous gas-stream simultaneous with the heating of the cold-trap. Furthermore, the volume of the material used to trap the labeled compound has been relative large in relation to the system to which the labeled compound has been transferred. Thus, the option of using this technique for radical concentration of the labeled compound and miniaturization of synthesis systems has not been explored. This is especially noteworthy in view of the fact that the amount of a $^{11}$C-labelled compound usually is in the range 20-60 nmol.

Recent technical development for the production and use of [$^{11}$C] carbon monoxide has made this compound useful in labeling synthesis. WO 02/102711 describes a system and a method for the production and use of a carbon-isotope monoxide enriched gas-mixture from an initial carbon-isotope dioxide gas mixture. [$^{11}$C] carbon monoxide may be obtained in high radiochemical yield from cyclotron produced [$^{11}$C] carbon dioxide and can be used to yield target compounds with high specific radioactivity. This reactor overcomes the difficulties listed above and is useful in synthesis of $^{11}$C-labelled compounds using [$^{11}$C] carbon monoxide in palladium or selenium mediated reaction. With such method, a broad array of carbonyl compounds can be labeled (Kihlberg, T.; Langstrom, B. J., Org. Chem. 1999, 9201-9205). The use of transition metal mediated reactions is, however, restricted by problems related to the competing β-hydride elimination reaction, which excludes or at least severely restricts utilization of organic electrophiles having hydrogen in β-position. Thus, a limitation of the transition metal mediated reactions is that most alkyl halides could not be used as substrates due to the β-hydride elimination reaction. One way to circumvent this problem is to use free-radical chemistry based on light irradiation of alkyl halides. However, this method gives poor results when weakly nucleophilic amines are used. Therefore, there is a need for a method in order to use photo-induced free radical carbonylation with weakly necleophilic amines to circumvent the problem with β-hydride elimination to complement the palladium mediated reactions and provide target structures to further increase the utility of [$^{11}$C] carbon monoxide in preparing useful PET tracers.

Discussion or citation of a reference herein shall not be construed as an admission that such reference is prior art to the present invention.

SUMMARY OF THE INVENTION

The present invention provides a method for labeling synthesis, comprising:

(a) providing a UV reactor assembly comprising a high pressure reaction chamber, a UV lamp and a concave mirror, wherein the high pressure reaction chamber having a window facing the concave mirror, a liquid inlet and a gas inlet in a bottom surface thereof, (b) reacting a solution of weakly nucleophilic amine with a metal base to improve the reactivity of said weakly nucleophilic amine, (c) adding a solution of akyl or aryl iodides to the solution of step (b) to give a reagent volume to be labeled, (d) introducing a carbon-isotope monoxide enriched gas-mixture into the reaction chamber of the UV reactor assembly via the gas inlet, (e) introducing at high-pressure said reagent volume into the reaction chamber via the liquid inlet, (f) turning on the UV lamp and waiting a predetermined time while the labeling synthesis occur, and (g) collecting the labeled amide from the reaction chamber.

The present invention also provides a system for labeling synthesis, comprising: a UV reactor assembly comprising a high pressure reaction chamber, a UV lamp and a concave mirror, wherein the high pressure reaction chamber having a window facing the concave mirror, a liquid inlet and a gas inlet in a bottom surface thereof, wherein the concave mirror can focus the UV light from the UV lamp, and the focused light beam enters the window of the reaction chamber.

The present invention further provides a method for the synthesis of labeled amides using photo-initiated carbonylation with [$^{11}$C] carbon monoxide using weakly nucleophilic amines treated with strong metal base and alkyl or aryl iodides.

In yet another embodiment, the invention also provides [$^{11}$C]-labeled amides. In still another embodiment, the invention provides kits for use as PET tracers comprising [$^{11}$C]-labeled amides.

DETAILED DESCRIPTION OF THE INVENTION

The object of the invention is to provide a method and a system for production of and use of carbon-isotope monoxide in labeling synthesis that overcomes the drawbacks of the prior art devices. This is achieved by the method and system claimed in the invention.

One advantage with such a method and system is that nearly quantitative conversion of carbon-isotope monoxide into labeled products can be accomplished.

There are several other advantages with the present method and system. The high-pressure technique makes it possible to use low boiling solvents such as diethyl ether at high temperatures (e.g. 200° C.). The use of a closed system consisting of materials that prevents gas diffusion, increases the stability of sensitive compounds and could be advantageous also with respect to Good Manufacturing Practice (GMP).

Still other advantages are achieved in that the resulting labeled compound is highly concentrated, and that the miniaturization of the synthesis system facilitates automation, rapid synthesis and purification, and optimization of specific radioactivity through minimization of isotopic dilution.

Most important is the opening of completely new synthesis possibilities, as exemplified by the present invention.

Embodiments of the invention will now be described with reference to the figures.

The term carbon-isotope that is used throughout this application preferably refers to $^{11}$C, but it should be understood that $^{11}$C may be substituted by other carbon-isotopes, such as $^{13}$C and $^{14}$C, if desired.

Figure 1:
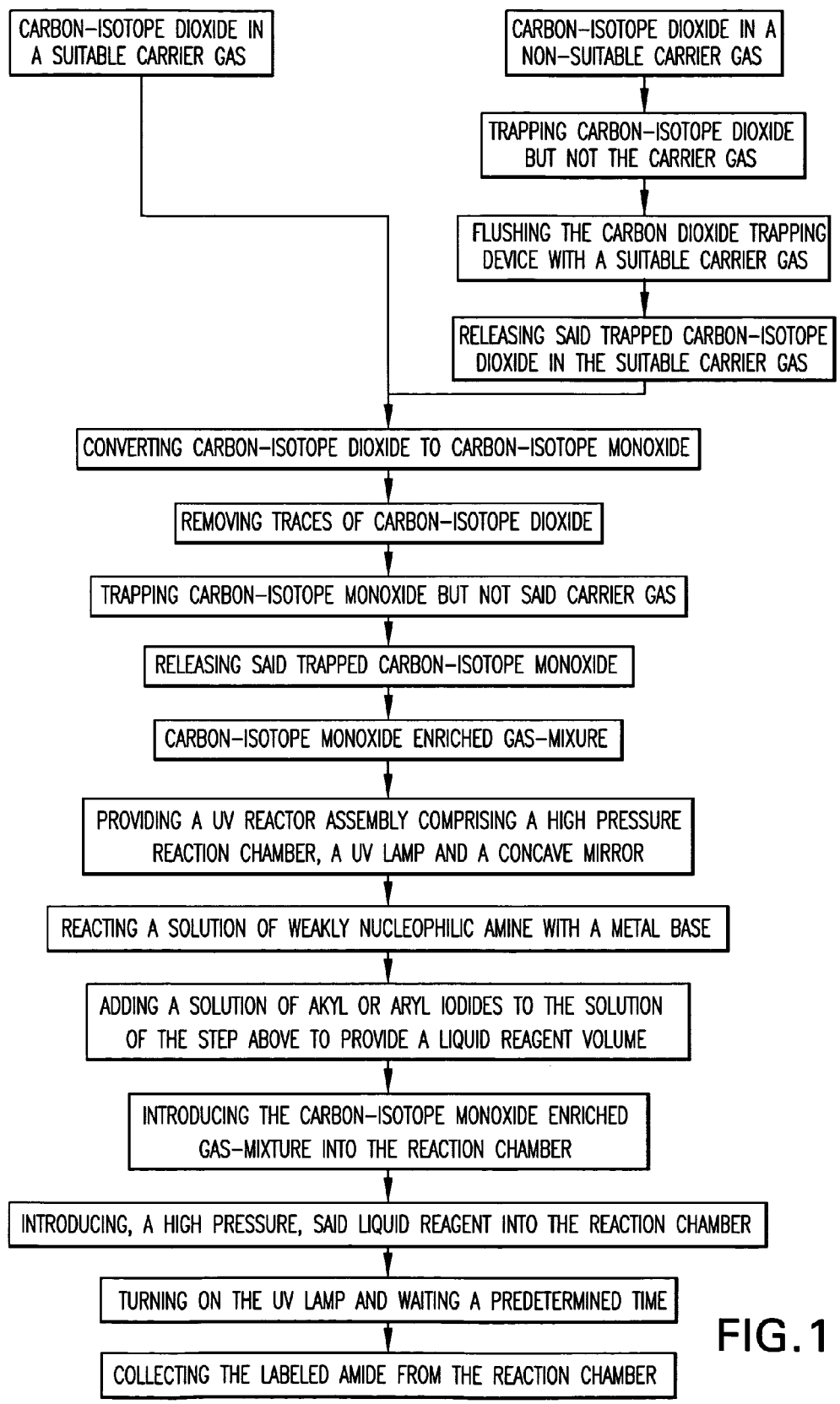
FIG. 1 shows a flow chart over the method according to the invention

FIG. 1 shows a flow chart over the method according to the invention, which firstly comprises production of a carbon-isotope monoxide enriched gas-mixture and secondly a labeling synthesis procedure. More in detail the production part of the method comprises the steps of:

Providing carbon-isotope dioxide in a suitable carrier gas of a type that will be described in detail below.

Converting carbon-isotope dioxide to carbon-isotope monoxide by introducing said gas mixture in a reactor device which will be described in detail below.

Removing traces of carbon-isotope dioxide by flooding the converted gas-mixture through a carbon dioxide removal device wherein carbon-isotope dioxide is trapped but not carbon-isotope monoxide nor the carrier gas, The carbon dioxide removal device will be described in detail below.

Trapping carbon-isotope monoxide in a carbon monoxide trapping device, wherein carbon-isotope monoxide is trapped but not said carrier gas. The carbon monoxide trapping device will be described in detail below.

Releasing said trapped carbon-isotope monoxide from said trapping device, whereby a volume of carbon-isotope monoxide enriched gas-mixture is achieved.

The production step may further comprise a step of changing carrier gas for the initial carbon-isotope dioxide gas mixture if the initial carbon-isotope dioxide gas mixture is comprised of carbon-isotope dioxide and a first carrier gas not suitable as carrier gas for carbon monoxide due to similar molecular properties or the like, such as nitrogen. More in detail the step of providing carbon-isotope dioxide in a suitable second carrier gas such as He, Ar, comprises the steps of:

Flooding the initial carbon-isotope dioxide gas mixture through a carbon dioxide trapping device, wherein carbon-isotope dioxide is trapped but not said first carrier gas. The carbon dioxide trapping device will be described in detail below.

Flushing said carbon dioxide trapping device with said suitable second carrier gas to remove the remainders of said first carrier gas.

Releasing said trapped carbon-isotope dioxide in said suitable second carrier gas.

The labeling synthesis step that may follow the production step utilizes the produced carbon-isotope dioxide enriched gas-mixture as labeling reactant. More in detail the step of labeling synthesis comprises the steps of:

Providing a UV reactor assembly comprising a UV lamp, a concave mirror and a high pressure reaction chamber having a liquid reagent inlet and a labeling reactant inlet in a bottom surface thereof. The UV reactor assembly and the reaction chamber will be described in detail below.

Providing a reagent volume that is to be labeled. The reagent volume can be prepared in following steps: 1. Dissolve an akyl or aryl iodide in a solvent; 2. Dissolve a weakly nucleophilic amine in a solvent in a separate vessel; 3. Add sufficient amount of metal base to the solution of weakly nucleophilic amine to increase the reactivity of said weakly nucleophilic amine; 4. Mix solutions of step 1 and step 3 to form a reagent volume as late as possible before being introduced into the reaction chamber. A "weakly nucleophic amine" is defined as an amine having a decay correlated radiochemical yield of less than 5% when react with an akyl or aryl iodide and $^{11}CO$ in a reaction without metal base. Definition and examples of metal base will be provided below.

Introducing the carbon-isotope monoxide enriched gas-mixture into the reaction chamber via the labeling reactant inlet.

Introducing, at high pressure, said liquid reagent into the reaction chamber via the liquid reagent inlet.

Turning on the UV lamp and waiting a predetermined time while the labeling synthesis occur.

Collecting the solution of labeled amide from the reaction chamber.

The step of waiting a predetermined time may further comprise adjusting the temperature of the reaction chamber such that the labeling synthesis is enhanced.

Figure 2:
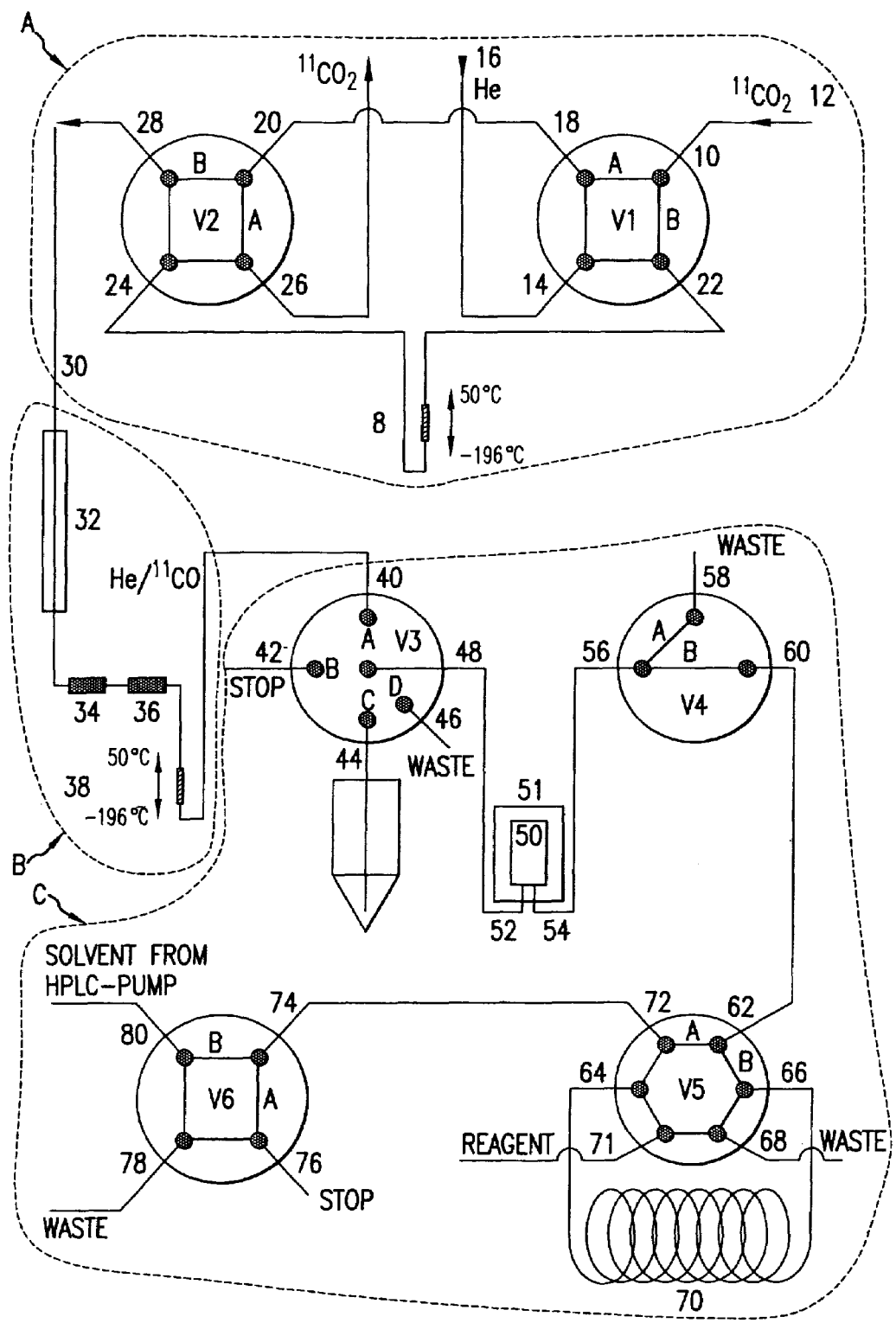
FIG. 2 is a schematic view of a carbon-isotope monoxide production and labeling-system according to the invention.

FIG. 2 schematically shows a [$^{11}C$]carbon dioxide production and labeling-system according to the present invention. The system is comprised of three main blocks, each handling one of the three main steps of the method of production and labeling:

Block A is used to perform a change of carrier gas for an initial carbon-isotope dioxide gas mixture, if the initial carbon-isotope dioxide gas mixture is comprised of carbon-isotope dioxide and a first carrier gas not suitable as carrier gas for carbon monoxide.

Block B is used to perform the conversion from carbon-isotope dioxide to carbon-isotope monoxide, and purify and concentrate the converted carbon-isotope monoxide gas mixture.

Block C is used to perform the carbon-isotope monoxide labeling synthesis.

Block A is normally needed due to the fact that carbon-isotope dioxide usually is produced using the $14N(p,\alpha)^{11}C$ reaction in a target gas containing nitrogen and 0.1% oxygen, bombarded with 17 MeV protons, whereby the initial carbon-isotope dioxide gas mixture comprises nitrogen as carrier gas. However, compared with carbon monoxide, nitrogen show certain similarities in molecular properties that makes it difficult to separate them from each other, e.g. in a trapping device or the like, whereby it is difficult to increase the concentration of carbon-isotope monoxide in such a gas mixture. Suitable carrier gases may instead be helium, argon or the like. Block A can also be used to change the pressure of the carrier gas (e.g. from 1 to 4 bar), in case the external system does not tolerate the gas pressure needed in block B and C. In an alternative embodiment the initial carbon-isotope dioxide gas mixture is comprised of carbon-isotope dioxide and a first carrier gas that is well suited as carrier gas for carbon monoxide, whereby the block A may be simplified or even excluded.

According to a preferred embodiment (FIG. 2), block A is comprised of a first valve V1, a carbon dioxide trapping device 8, and a second valve V2.

The first valve V1 has a carbon dioxide inlet 10 connected to a source of initial carbon-isotope dioxide gas mixture 12, a carrier gas inlet 14 connected to a source of suitable carrier gas 16, such as helium, argon and the like. The first valve V1 further has a first outlet 18 connected to a first inlet 20 of the second valve V2, and a second outlet 22 connected to the carbon dioxide trapping device 8. The valve V1 may be operated in two modes A, B, in mode A the carbon dioxide inlet 10 is connected to the first outlet 18 and the carrier gas inlet 14 is connected to the second outlet 22, and in mode B the carbon dioxide inlet 10 is connected to the second outlet 22 and the carrier gas inlet 14 is connected to the first outlet 18.

In addition to the first inlet 20, the second valve V2 has a second inlet 24 connected to the carbon dioxide trapping device 8. The second valve V2 further has a waste outlet 26, and a product outlet 28 connected to a product inlet 30 of block B. The valve V2 may be operated in two modes A, B, in mode A the first inlet 20 is connected to the waste outlet 26 and the second inlet 24 is connected to the product outlet 28, and in mode B the first inlet 20 is connected to the product outlet 28 and the second inlet 24 is connected to the waste outlet 26.

The carbon dioxide trapping device 8 is a device wherein carbon dioxide is trapped but not said first carrier gas, which trapped carbon dioxide thereafter may be released in a controlled manner. This may preferably be achieved by using a cold trap, such as a column containing a material which in a cold state, (e.g. $-196°$ C. as in liquid nitrogen or $-186°$ C. as in liquid argon) selectively trap carbon dioxide and in a warm state (e.g. $+50°$ C.) releases the trapped carbon dioxide. (In this text the expression "cold trap" is not restricted to the use of cryogenics. Thus, materials that traps the topical compound at room temperature and release it at a higher temperature are included). One suitable material is porapac Q®. The trapping behavior of a porapac-column is related to dipole-dipole interactions or possibly Van der Waal interaktions. The said column 8 is preferably formed such that the volume of the trapping material is to be large enough to efficiently trap (>95%) the carbon-isotope dioxide, and small enough not to prolong the transfer of trapped carbon dioxide to block B. In the case of porapac Q® and a flow of 100 ml nitrogen/min, the volume should be 50-150 µl. The cooling and heating of the carbon dioxide trapping device 8 may further be arranged such that it is performed as an automated process, e.g. by automatically lowering the column into liquid nitrogen and moving it from there into a heating arrangement.

According to the preferred embodiment of FIG. 2 block B is comprised of a reactor device 32 in which carbon-isotope dioxide is converted to carbon-isotope monoxide, a carbon dioxide removal device 34, a check-valve 36, and a carbon monoxide trapping device 38, which all are connected in a line.

In the preferred embodiment the reactor device 32 is a reactor furnace comprising a material that when heated to the right temperature interval converts carbon-isotope dioxide to carbon-isotope monoxide. A broad range of different materials with the ability to convert carbon dioxide into carbon monoxide may be used, e.g. zinc or molybdenum or any other element or compound with similar reductive properties. If the reactor device 32 is a zinc furnace it should be heated to 400°

C., and it is important that the temperature is regulated with high precision. The melting point of zinc is 420° C. and the zinc-furnace quickly loses it ability to transform carbon dioxide into carbon monoxide when the temperature reaches over 410° C., probably due to changed surface properties. The material should be efficient in relation to its amount to ensure that a small amount can be used, which will minimize the time needed to transfer radioactivity from the carbon dioxide trapping device 8 to the subsequent carbon monoxide trapping device 38. The amount of material in the furnace should be large enough to ensure a practical life-time for the furnace (at least several days). In the case of zinc granulates, the volume should be 100-1000 µl.

The carbon dioxide removal device 34 is used to remove traces of carbon-isotope dioxide from the gas mixture exiting the reactor device 32. In the carbon dioxide removal device 34, carbon-isotope dioxide is trapped but not carbon-isotope monoxide nor the carrier gas. The carbon dioxide removal device 34 may be comprised of a column containing ascarite® (i.e. sodium hydroxide on silica). Carbon-isotope dioxide that has not reacted in the reactor device 32 is trapped in this column (it reacts with sodium hydroxide and turns into sodium carbonate), while carbon-isotope monoxide passes through. The radioactivity in the carbon dioxide removal device 34 is monitored as a high value indicates that the reactor device 32 is not functioning properly.

Like the carbon dioxide trapping device 8, the carbon monoxide trapping device 38, has a trapping and a releasing state. In the trapping state carbon-isotope monoxide is selectively trapped but not said carrier gas, and in the releasing state said trapped carbon-isotope monoxide is released in a controlled manner. This may preferably be achieved by using a cold trap, such as a column containing silica which selectively trap carbon monoxide in a cold state below −100° C., e.g. −196° C. as in liquid nitrogen or −186° C. as in liquid argon, and releases the trapped carbon monoxide in a warm state (e.g. +50° C.). Like the porapac-column, the trapping behavior of the silica-column is related to dipole-dipole interactions or possibly Van der Waal interactions. The ability of the silica-column to trap carbon-isotope monoxide is reduced if the helium, carrying the radioactivity, contains nitrogen. A rationale is that since the physical properties of nitrogen are similar to carbon monoxide, nitrogen competes with carbon monoxide for the trapping sites on the silica.

According to the preferred embodiment of FIG. 2, block C is comprised of a first and a second reaction chamber valve V3 and V4, a reagent valve V5, an injection loop 70 and a solvent valve V6, and the UV reactor assembly 51 which comprises a UV lamp 91, a concave mirror 92 and a reaction chamber 50.

The first reaction chamber valve V3 has a gas mixture inlet 40 connected to the carbon monoxide trapping device 38, a stop position 42, a collection outlet 44, a waste outlet 46, and a reaction chamber connection port 48 connected to a gas inlet 52 of the reaction chamber 50. The first reaction chamber valve V3 has four modes of operation A to D. The reaction chamber connection port 48 is: in mode A connected to the gas mixture inlet 40, in mode B connected to the stop position 42, in mode C connected to the collection outlet 44, and in mode D connected to the waste outlet 46.

Figure 3:
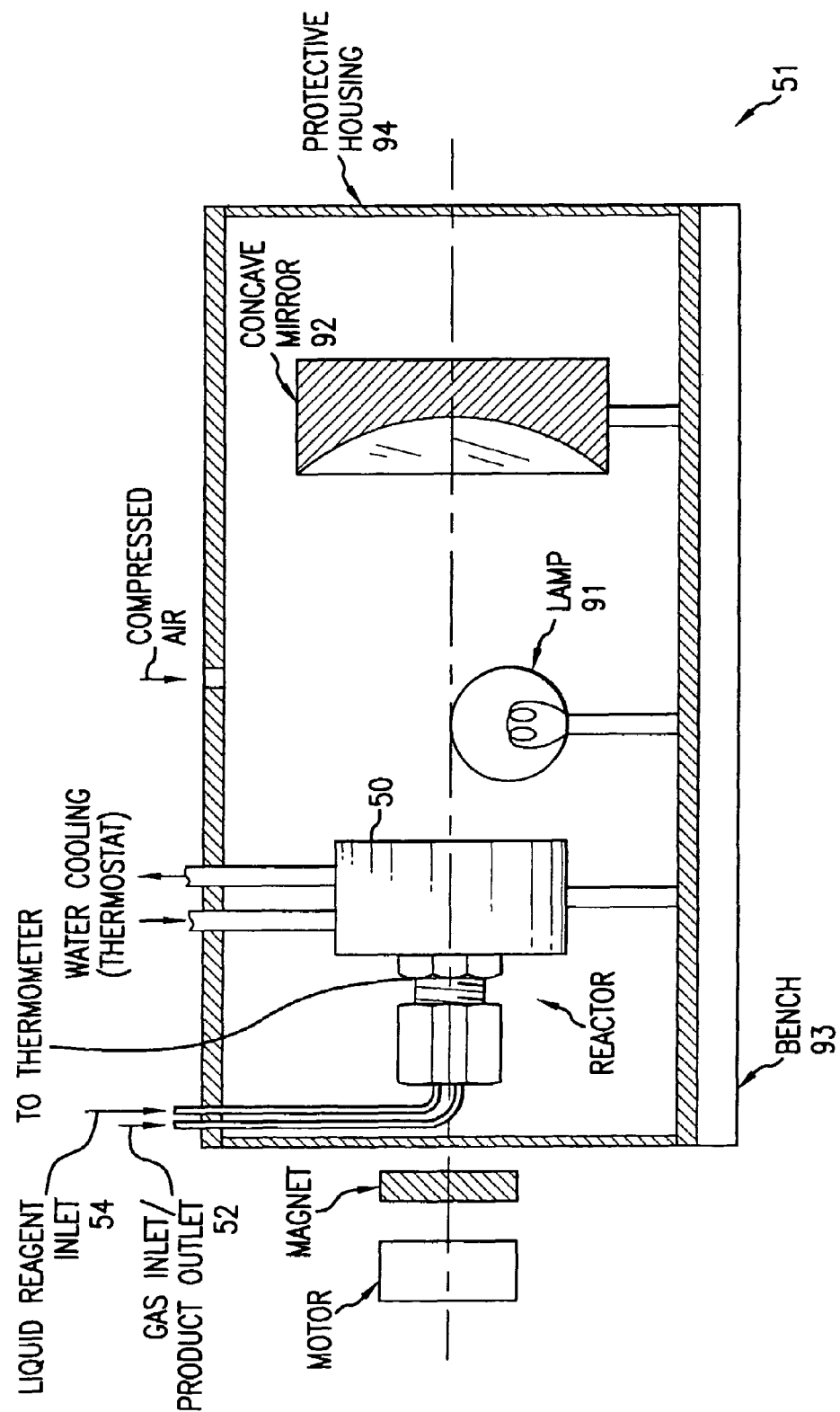
FIG. 3 shows the main parts of the UV reactor assembly.

FIG. 3 is a diagram of UV reactor assembly 51. It comprises of a UV lamp 91, a concave mirror 92, a reaction chamber 50. In a preferred embodiment, it also includes a bench 93 and protective housing 94, so that all parts located inside of the protective housing and mounted on the bench. In the most preferred embodiment, it further comprises a motor 95, a magnet stirrer 96, a magnet stirring bar 97 and a thermocouple 98 (see FIG. 5).

In a preferred embodiment, all parts are mounted on a bench. They are shielded with a thin protective housing outside for protection against LV radiation. Compressed air is supplied through inlet attached to the top face of the housing to ventilate the device and to provide normal operation conditions for the LV lamp.

Figure 4:
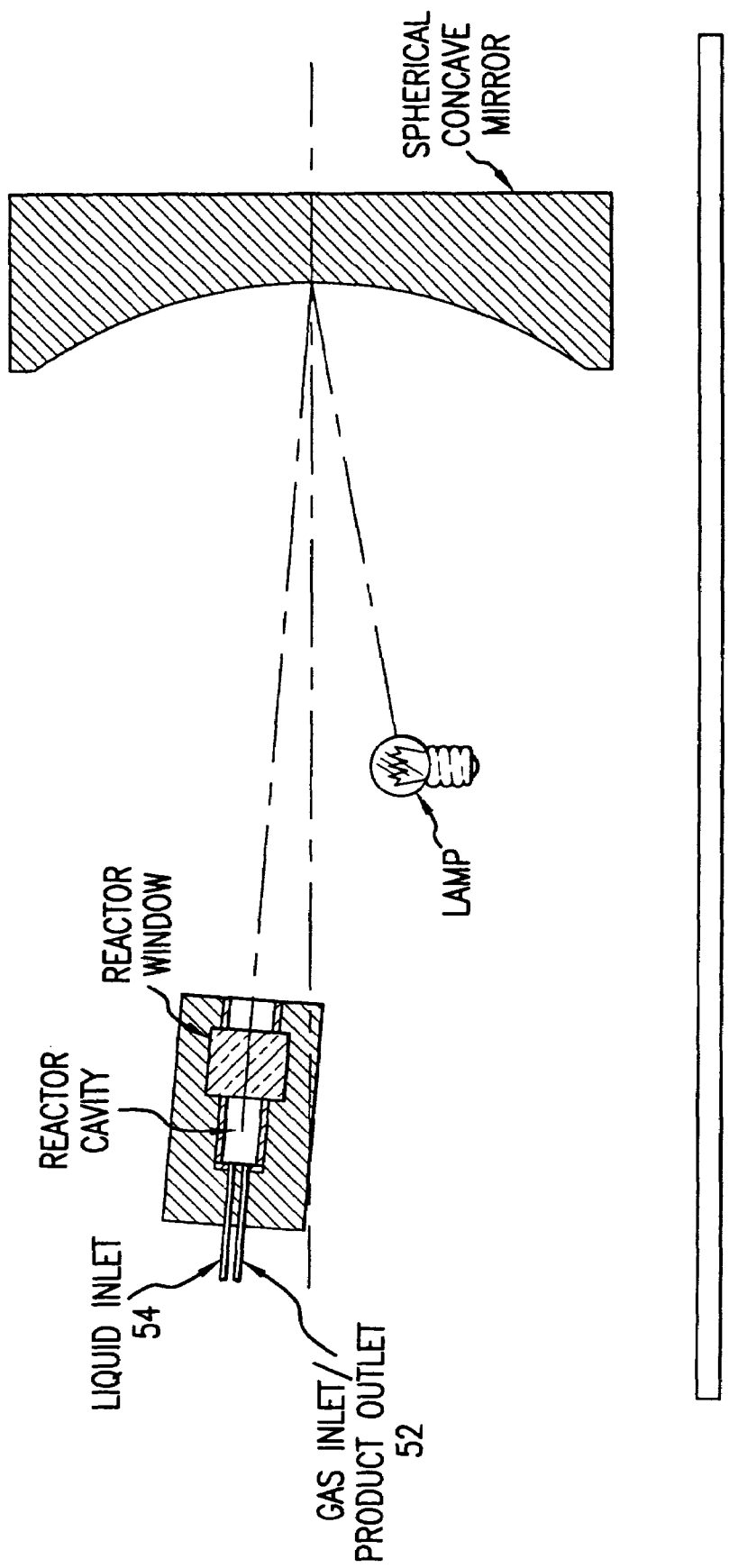
FIG. 4 is the schematic diagram of the optical scheme of the UV reactor assembly.

The optical scheme is illustrated in FIG. 4. A spherical concave mirror is used to collect the output of the arc and direct it onto the reactor cavity. The light source and reactor are displaced from the optical axis of the mirror so that the UV lamp does not block the light collected by the mirror. This also prevents the bulb from overheating. Distance between the reactor and the lamp is kept at minimum to ensure smallest arc image.

Figure 7A:
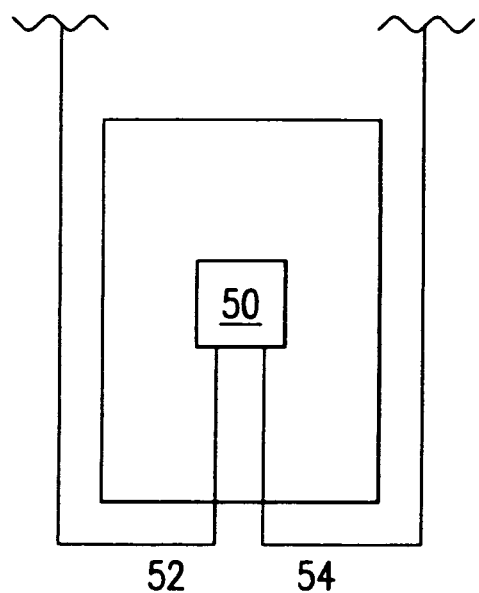
FIGS. 7a and 7b show alternative embodiments of a reaction chamber according to the invention.
Figure 7B:
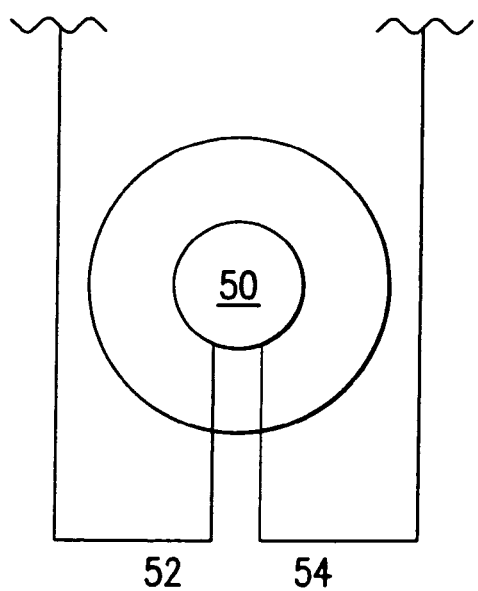

The reaction chamber 50 (micro-autoclave) has a gas inlet 52 and a liquid inlet 54, which are arranged such that they terminate at the bottom surface of the chamber. Gas inlet 52 may also be used as product outlet after the labeling is finished. During operation the carbon-isotope monoxide enriched gas mixture is introduced into the reaction chamber 50 through the gas inlet 52, where after the liquid reagent at high pressure enters the reaction chamber 50 through the liquid inlet 54. FIGS. 3*a* and 3*b* shows schematic views of two preferred reaction chambers 50 in cross section. FIG. 7*a* is a cylindrical chamber which is fairly easy to produce, whereas the spherical chamber of FIG. 7*b* is the most preferred embodiment, as the surface area to volume-ratio of the chamber is further minimized. A minimal surface area to volume-ratio optimizes the recovery of labeled product and minimizes possible reactions with the surface material. Due to the "diving-bell construction" of the reaction chamber 50, both the gas inlet 52 and the liquid inlet 54 becomes liquid-filled and the reaction chamber 50 is filled from the bottom upwards. The gas-volume containing the carbon-isotope monoxide is thus trapped and given efficient contact with the reaction mixture. Since the final pressure of the liquid is approximately 80 times higher than the original gas pressure, the final gas volume will be less than 2% of the liquid volume according to the general gas-law. Thus, a pseudo one-phase system will result. In the instant application, the term "pseudo one-phase system" means a closed volume with a small surface area to volume-ratio containing >96% liquid and <4% gas at pressures exceeding 200 bar. In most syntheses the transfer of carbon monoxide from the gas-phase to the liquid phase will probably not be the rate limiting step. After the labeling is finished the labeled volume is nearly quantitatively transferred from the reaction chamber by the internal pressure via the gas inlet/product outlet 52 and the first reaction chamber valve V3 in position C.

Figure 5:
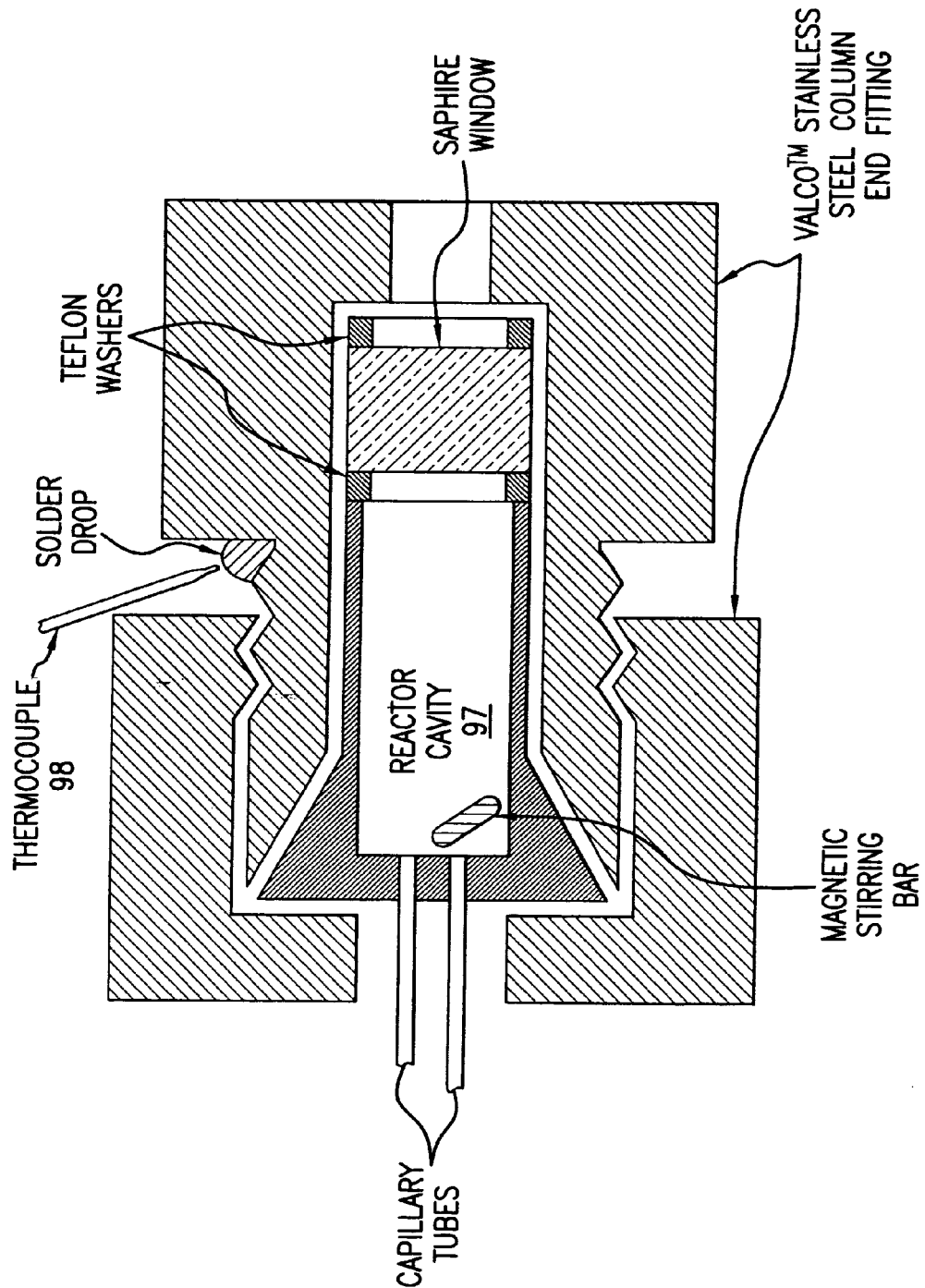
FIG. 5 is the cross-sectional view of the reaction chamber.

In a specific embodiment, FIG. 5 shows a reaction chamber made from stainless steel (Valco™) column end fitting. It is equipped with sapphire window, which is a hard material transparent to short wavelength UV radiation. The window is pressed between two Teflon washers inside the drilled column end fitting to make the reactor tight at high pressures. Temperature measurement can be accomplished with the thermocouple 98 attached by solder drop to the outer side of the reactor. The magnet stirrer drives small Teflon coated magnet place inside the reaction chamber. The magnetic stirrer can be attached to the side of the reaction chamber in the assembly. Distance between the magnet stirrer and the reactor should be minimal.

Figure 6:
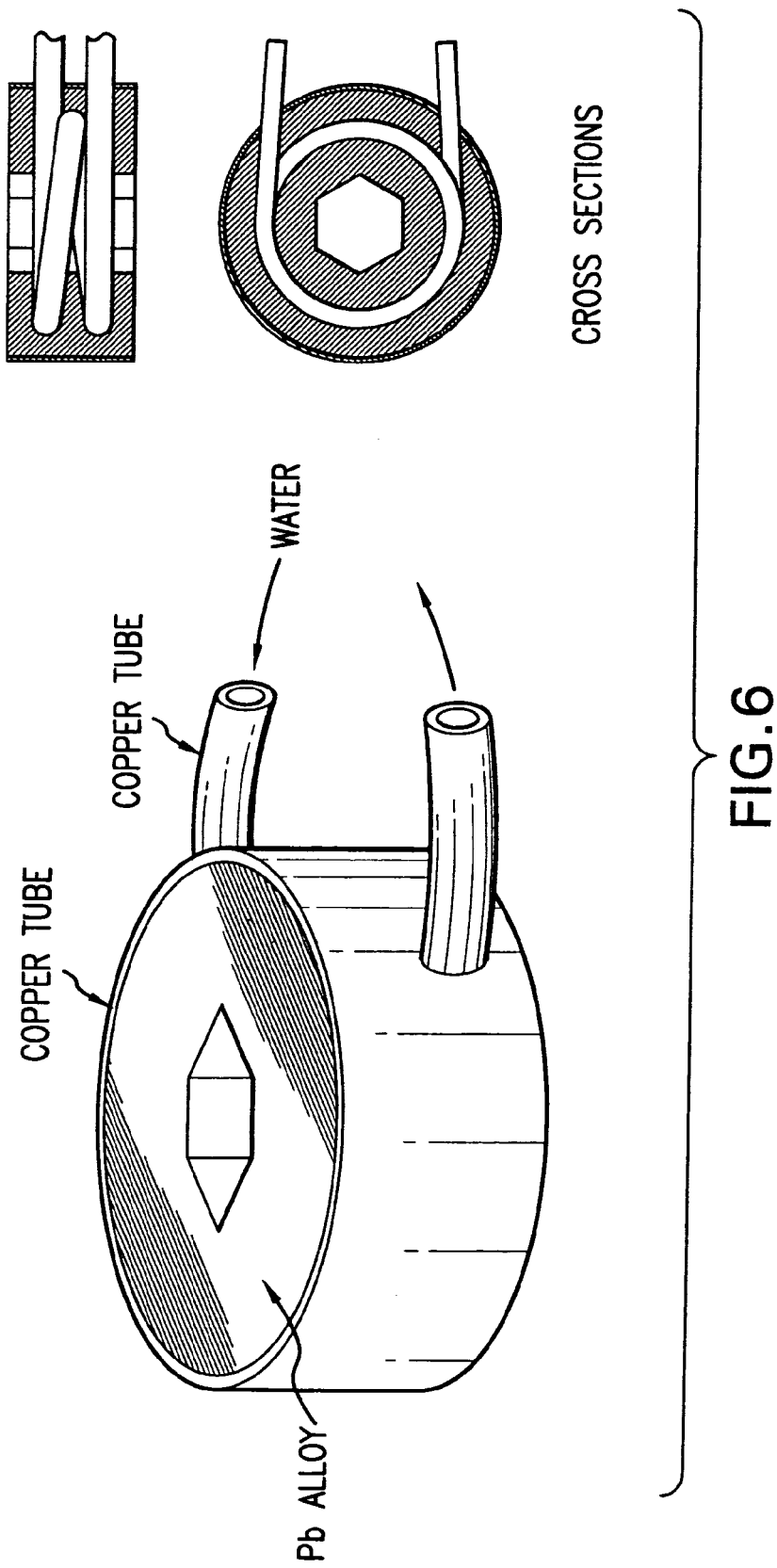
FIG. 6 shows reaction chamber and its cooling jacket.

FIG. 6 illustrates a device used to remove excessive heat produced by the light source and keep the reaction chamber at constant temperature. Copper tube can be placed into the short piece of copper tube of larger diameter filled up with lead alloy. Hexagonal hole can be made to fit the reaction chamber nut tightly. To increase heat transfer between reactor and the thermostat, thermoconductive silicon grease can be used. The thermostat can then be connected to standalone water bath thermostat with rubber tubes.

Referring back to FIG. 2, the second reaction chamber valve V4 has a reaction chamber connection port 56, a waste outlet 58, and a reagent inlet 60. The second reaction chamber valve V4 has two modes of operation A and B. The reaction chamber connection port 56 is: in mode A connected to the waste outlet 58, and in mode B it is connected to the reagent inlet 60.

The reagent valve V5, has a reagent outlet 62 connected to the reagent inlet 60 of the second reaction chamber valve V4, an injection loop inlet 64 and outlet 66 between which the injection loop 70 is connected, a waste outlet 68, a reagent inlet 71 connected to a reagent source, and a solvent inlet 72. The reagent valve V5, has two modes of operation A and B. In mode A the reagent inlet 71 is connected to the injection loop inlet 64, and the injection loop outlet 66 is connected to the waste outlet 68, whereby a reagent may be fed into the injection loop 70. In mode B the solvent inlet 72 is connected to the injection loop inlet 64, and the injection loop outlet 66 is connected to the reagent outlet 62, whereby reagent stored in the injection loop 70 may be forced via the second reaction chamber valve V4 into the reaction chamber 50 if a high pressure is applied on the solvent inlet 72.

The solvent valve V6, has a solvent outlet 74 connected to the solvent inlet 72 of the reagent valve V5, a stop position 76, a waste outlet 78, and a solvent inlet 80 connected to a solvent supplying HPLC-pump (High Performance Liquid Chromatography) or any liquid-pump capable of pumping organic solvents at 0-10 ml/min at pressures up to 400 bar (not shown). The solvent valve V6, has two modes of operation A and B. In mode A the solvent outlet 74 is connected to the stop position 76, and the solvent inlet 80 is connected to the waste outlet 78. In mode B the solvent outlet 74 is connected to the solvent inlet 80, whereby solvent may be pumped into the system at high pressure by the HPLC-pump.

Except for the small volume of silica in the carbon monoxide trapping devise 38, an important difference in comparison to the carbon dioxide trapping device 8, as well as to all related prior art, is the procedure used for releasing the carbon monoxide. After the trapping of carbon monoxide on carbon monoxide trapping devise 8, valve V3 is changed from position A to B to stop the flow from the carbon monoxide trapping devise 38 and increase the gas-pressure on the carbon monoxide trapping devise 38 to the set feeding gas pressure (3-5 bar). The carbon monoxide trapping devise 38 is then heated to release the carbon monoxide from the silica surface while not significantly expanding the volume of carbon monoxide in the carrier gas. Valve V4 is changed from position A to B and valve V3 is then changed from position B to A. At this instance the carbon monoxide is rapidly and almost quantitatively transferred in a well-defined micro-plug into the reaction chamber 50. Micro-plug is defined as a gas volume less than 10% of the volume of the reaction chamber 50, containing the topical substance (e.g. 1-20 μL). This unique method for efficient mass-transfer to a small reaction chamber 50, having a closed outlet, has the following prerequisites:

A micro-column 38 defined as follows should be used. The volume of the trapping material (e.g. silica) should be large enough to efficiently trap (>95%) the carbon-isotope monoxide, and small enough (<1% of the volume of a subsequent reaction chamber 50) to allow maximal concentration of the carbon-isotope monoxide. In the case of silica and a reaction chamber 50 volume of 200 μl, the silica volume should be 0.1-2 μl.

The dead volumes of the tubing and valve(s) connecting the silica column and the reaction chamber 50 should be minimal (<10% of the micro-autoclave volume).

The pressure of the carrier gas should be 3-5 times higher than the pressure in the reaction chamber 50 before transfer (1 atm.).

In one specific preferred embodiment specifications, materials and components are chosen as follows. High pressure valves from Valco®, Reodyne® or Cheminert® are used. Stainless steel tubing with o.d. 1/16" is used except for the connections to the porapac-column 8, the silica-column 38 and the reaction chamber 50 where stainless steel tubing with o.d. 1/32" are used in order to facilitate the translation movement. The connections between V1, V2 and V3 should have an inner diameter of 0.2-1 mm. The requirement is that the inner diameter should be large enough not to obstruct the possibility to achieve the optimal flow of He (2-50 ml/min) through the system, and small enough not to prolong the time needed to transfer the radioactivity from the porapac-column 8 to the silica-column 38. The dead volume of the connection between V3 and the autoclave should be minimized (<10% of the autoclave volume). The inner diameter (0.05-0.1 mm) of the connection must be large enough to allow optimal He flow (2-50 ml/min). The dead volume of the connection between V4 and V5 should be less than 10% of the autoclave volume.

The porapac-column 8 preferably is comprised of a stainless steel tube (o.d.=1/8", i.d.=2 mm, l=20 mm) filled with Porapac Q® and fitted with stainless steel screens. The silica-column 38 preferably is comprised of a stainless steel tube (o.d.=1/16", i.d.=0.1 mm) with a cavity (d=1 mm, h=1 mm, V=0.8 μl) in the end. The cavity is filled with silica powder (100/80 mesh) of GC-stationary phase type. The end of the column is fitted against a stainless steel screen.

It should be noted that a broad range of different materials could be used in the trapping devices. If a GC-material is chosen, the criterions should be good retardation and good peak-shape for carbon dioxide and carbon monoxide respectively. The latter will ensure optimal recovery of the radioactivity.

Below a detailed description is given of a method of producing carbon-isotope using an exemplary system as described above.

Preparations of the system are performed by the steps 1 to 5:

1. V1 in position A, V2 in position A, V3 in position A, V4 in position A, helium flow on with a max pressure of 5 bar. With this setting, the helium flow goes through the porapac column, the zinc furnace, the silica column, the reaction chamber 50 and out through V4. The system is conditioned, the reaction chamber 50 is rid of solvent and it can be checked that helium can be flowed through the system with at least 10 ml/min. UV lamp 91 is turned on.
2. The zinc-furnace is turned on and set at 400° C.
3. The porapac- and silica-columns are cooled with liquid nitrogen. At −196° C., the porapac- and silica-column efficiently traps carbon-isotope dioxide and carbon-isotope monoxide respectively.
4. V5 in position A (load). The injection loop (250 μl), attached to V5, is loaded with the reaction mixture.
5. The HPLC-pump is attached to a flask with freshly distilled THF (or other high quality solvent) and primed. V6 in position A.

Production of carbon-isotope dioxide may be performed by the steps 6 to 7:

6. Carbon-isotope dioxide is produced using the 14N(p,α) $^{11}$C reaction in a target gas containing nitrogen (AGA, Nitrogen 6.0) and 0.1% oxygen (AGA. Oxygen 4.8), bombarded with 17 MeV protons.

7. The carbon-isotope dioxide is transferred to the apparatus using nitrogen with a flow of 100 m/min.

Synthesis of carbon-isotope may thereafter be performed by the steps 8 to 16

8. V1 in position B and V2 in position B. The nitrogen flow containing the carbon-isotope dioxide is now directed through the porapac-column (cooled to −196° C.) and out through a waste line. The radioactivity trapped in the porapac-column is monitored.

9. When the radioactivity has peaked, V1 is changed to position A. Now a helium flow is directed through the porapac-column and out through the waste line. By this operation the tubings and the porapac-column are rid of nitrogen.

10. V2 in position A and the porapac-column is warmed to about 50° C. The radioactivity is now released from the porapac-column and transferred with a helium flow of 10 ml/min into the zinc-furnace where it is transformed into carbon-isotope monoxide.

11. Before reaching the silica-column (cooled to −196° C.), the gas flow passes the ascarite-column. The carbon-isotope monoxide is now trapped on the silica-column. The radioactivity in the silica-column is monitored and when the value has peaked, V3 is set to position B and then V4 is set to position B.

12. The silica-column is heated to approximately 50° C., which releases the carbon-isotope monoxide. V3 is set to position A and the carbon-isotope monoxide is transferred to the reaction chamber 50 within 15 s.

13. V3 is set to position B, V5 is set to position B, the HPLC-pump is turned on (flow 7 ml/min) and V6 is set to position B. Using the pressurised THF (or other solvent), the reaction mixture is transferred to the reaction chamber 50. When the HPLC-pump has reached its set pressure limit (e.g. 40 Mpa), it is automatically turned off and then V6 is set to position A.

14. Motor 95, magnetic stir 96 and magnet stirring bar 97 in reaction chamber 50 are turned on.

15. After a sufficient reaction-time (usually 5 min), V3 is set to position C and the content of the reaction chamber 50 is transferred to a collection vial.

16. The reaction chamber 50 can be rinsed by the following procedure: V3 is set to position B, the HPLC-pump is turned on, V6 is set to position B and when maximal pressure is reached V6 is set to position A and V3 is set to position 3 thereby transferring the rinse volume to the collection vial.

With the recently developed fully automated version of the reaction chamber 50 system according to the invention, the value of [$^{11}$C]carbon monoxide as a precursor for $^{11}$C-labelled tracers has become comparable with [$^{11}$C]methyl iodide. Currently, [$^{11}$C]methyl iodide is the most frequently used $^{11}$C-precursor due to ease in production and handling and since groups suitable for labeling with [$^{11}$C]methyl iodide (e.g. hetero atom bound methyl groups) are common among biologically active substances. Carbonyl groups, that can be conveniently labeled with [$^{11}$C]carbon monoxide, are also common among biologically active substances. In many cases, due to metabolic events in vivo, a carbonyl group may even be more advantageous than a methyl group as labeling position. The use of [$^{11}$C]carbon monoxide for production of PET-tracers may thus become an interesting complement to [$^{11}$C]methyl iodide. Furthermore, through the use of similar technology, this method will most likely be applicable for synthesis of $^{13}$C and $^{14}$C substituted compounds.

The main advantage of the present invention is to overcome the limitations of radical-mediated reaction to synthesize $^{11}$C-labeled amides using alkyl/aryl iodides and weakly nucleophilic amines as precursors. The levels specific radioactivity are high compared with alternative methods such as the use of Grignard reactions for preparation of [carbonyl-$^{11}$C] amides. Amines used as precursors in the instant invention have a formula

wherein R' and R" are independently H, linear or cyclic alkyl or substituted alkyl, aryl or substituted aryl, and may contain chloro or fluoro groups. Examples of weakly nucleophic amines applicable to the instant invention include diphenylamine, indole and 5H-Dibenzo[b,f]azepine. Metal base used in the instant invention is defined as MB, wherein M is selected from the list comprising Li, Na, K, Cs and Mg, and B can be alkyl, aryl, hydride, dicyclohexylamide, diisopropylamide, hexamethyldisilylamide or YMGX, wherein Y=alkyl, aryl and X=halogen (Cl, Br and I). Examples of metal base include alkyl lithium, lithium bis(trimethylsilyl)amide, sodium hydride and Na diisopropyl amide. Iodides used in this invention have a formula RI, where R is linear or cyclic alkyl or substituted alkyl, aryl or substituted aryl, and may contain chloro, fluoro groups. The resultant labeled amides have a formula

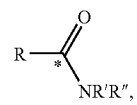

wherein R, R' and R" are defined as above. They provide valuable PET tracers in various PET studies. In an embodiment of the present invention, it provides kits for use as PET tracers comprising [$^{11}$C]-labeled amides.

Such kits are designed to give sterile products suitable for human administration, e.g. direct injection into the bloodstream. Suitable kits comprise containers (e.g. septum-sealed vials).

The kits may optionally further comprise additional components such as radioprotectant, antimicrobial preservative, pH-adjusting agent or filler.

By the term "radioprotectant" is meant a compound which inhibits degradation reactions, such as redox processes, by trapping highly-reactive free radicals, such as oxygen-containing free radicals arising from the radiolysis of water. The radioprotectants of the present invention are suitably chosen from: ascorbic acid, para-aminobenzoic acid (i.e. 4-aminobenzoic acid), gentisic acid (i.e. 2,5-dihydroxybenzoic acid) and salts thereof with a biocompatible.

By the term "antimicrobial preservative" is meant an agent which inhibits the growth of potentially harmful micro-organisms such as bacteria, yeasts or moulds. The antimicrobial preservative may also exhibit some bactericidal properties, depending on the dose. The main role of the antimicrobial preservative(s) of the present invention is to inhibit the growth of any such micro-organism in the pharmaceutical composition post-reconstitution, i.e. in the radioactive diagnostic product itself. The antimicrobial preservative may, however, also optionally be used to inhibit the growth of potentially harmful micro-organisms in one or more components of the kit of the present invention prior to reconstitution. Suitable antimicrobial preservatives include: the parabens, i.e., ethyl, propyl or butyl paraben or mixtures thereof; benzyl alcohol; phenol; cresol; cetrimide and thiomersal. Preferred antimicrobial preservative(s) are the parabens.

The term "pH-adjusting agent" means a compound or mixture of compounds useful to ensure that the pH of the reconstituted kit is within acceptable limits (approximately pH 4.0 to 10.5) for human administration. Suitable such pH-adjusting agents include pharmaceutically acceptable buffers, such as tricine, phosphate or TRIS [i.e. tris(hydroxymethyl)aminomethane], and pharmaceutically acceptable bases such as sodium carbonate, sodium bicarbonate or mixtures thereof. When the ligand conjugate is employed in acid salt form, the pH-adjusting agent may optionally be provided in a separate vial or container, so that the user of the kit can adjust the pH as part of a multi-step procedure.

By the term "filler" is meant a pharmaceutically acceptable bulking agent which may facilitate material handling during production and lyophilisation. Suitable fillers include inorganic salts such as sodium chloride, and water soluble sugars or sugar alcohols such as sucrose, maltose, mannitol or trehalose.

General reaction scheme for the synthesis of labeled amides are as illustrated below:

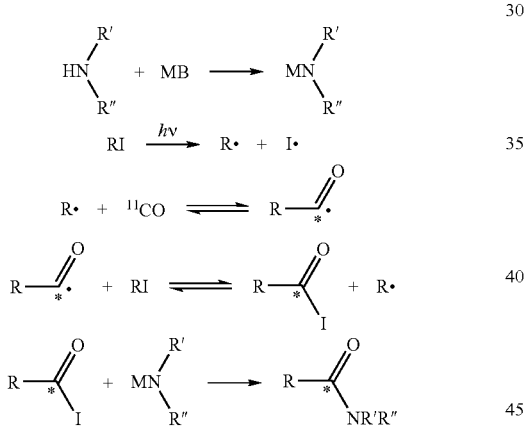

wherein R, R', R" and MB are as defined above. * indicates the $^{11}$C labeled position.

EXAMPLES

The invention is further described in the following examples which are in no way intended to limit the scope of the invention.

Example 1

Precursors and Resultant Products

The following experiments illustrate the present invention. Radical carbonylation using submicromolar amounts of [$^{11}$C] carbon monoxide is performed yielding labeled with the amides shown in Table 1 as target compounds.

Weakly nucleophic amines and alkyl iodides used for the labeling are shown in List 1 and List 2 respectively. Labelled amides according to the instant invention is shown in List 3.

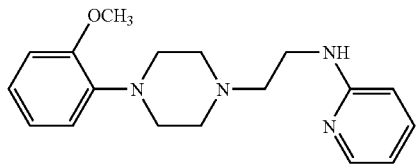

{2-[4-(2-Methoxy-phenyl)-piperazin-1-yl]-ethyl}-pyridin-2-yl-amine

WAY-100634

List 1. Weakly nucleophilic amine used in labeling.

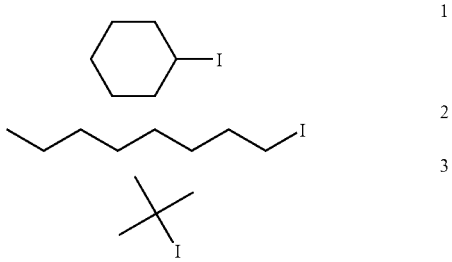

List 2. Iodides used as precursors in labeling.

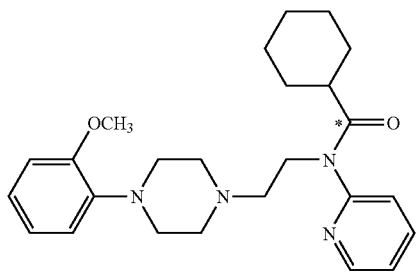

compound 4, * indicates $^{11}$C labeled position

[carbonyl-$^{11}$C]Cyclohexanecarboxylic acid {2-[4-(2-methoxy-phenyl)-piperazin-1-yl]-ethyl}-pyridin-2-yl-amide

WAY-100635

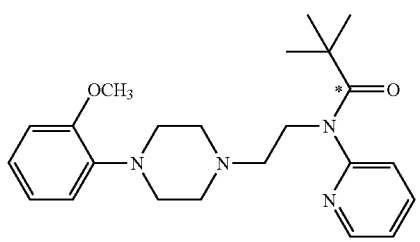

compound 5, * indicates $^{11}$C labeled position

[carbonyl-$^{11}$C]N-{2-[4-(2-Methoxy-phenyl)-piperazin-1-yl]-ethyl}-2,2-dimethyl-N-pyridin-2-yl-propionamide

WAY-100135

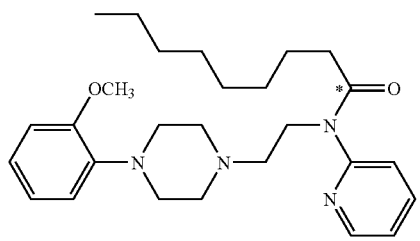

compound 6, * indicates $^{11}$C labeled position

[carbonyl-$^{11}$C]Nonanoic acid {2-[4-(2-methoxy-phenyl)-piperazin-1-yl]-ethyl}-pyridin-2-yl-amide List 3. Labelled amides according to the instant invention.

Initial experiments performed by the standard procedure described below afforded only 2% decay corrected radiochemical yield (determined by LC) of the $^{11}$C-carbonyl labelled WAY-100635 and a number of radiolabelled by-products. The reactions were carried out in a 270 μl stainless steel reaction vessel equipped with a sapphire window. The reactor was filled with [$^{11}$C]carbon monoxide in helium. Then the solution of an alkyl iodide together with the amine was pressurized at 35 MPa and reaction mixture was irradiated with focused light from a medium pressure Hg lamp (400 W) during 400 s. After the synthesis the crude mixture was collected in a vial. The amount of [$^{11}$C]carbon monoxide consumed in the reaction was estimated by measurements of radioactivity before and after purge of the gas phase in the collection vial. A sample from the crude reaction mixture was withdrawn for HPLC analysis and the remaining material was purified by semi-preparative HPLC.

In order to increase the reactivity of the amine it was treated with different strong bases before the reaction with [11C] carbon monoxide. NaHDMS provided the best radiochemical yield and highest conversion of [11C]carbon monoxide (Table 1, entry 5).

Two related compounds were labelled with the same method: WAY-100135 and a nonanoyl analogue (Table 1, entries 6-8).

TABLE 1

Trapping efficiency and radiochemical yields of $^{11}$C-labeled amides.

| Entry | Product | Base | Conversion of carbon monoxide,$^a$ % | Yield,$^b$ % |
|---|---|---|---|---|
| 1 | WAY-100635 (4) | t-BuLi | 91 (94) | 46$^c$ (38$^c$) |
| 2 | WAY-100635 (4) | NaH | 17 | 3$^c$ |
| 3 | WAY-100635 (4) | LDA | 91 | 29$^c$ |
| 4 | WAY-100635 (4) | KHDMS | 39 | 8$^c$ |
| 5 | WAY-100635 (4) | NaHDMS | 91 (91) | 62 (55) |
| 6 | WAY-100135 (5) | NaHDMS | 28 | 9$^c$ |
| 7 | Octyl WAY (6) | NaHDMS | 41 | 12 |
| 8 | Octyl WAY (6) | LiHDMS | 70 | 22$^c$ |

$^a$Decay-corrected, the fraction of radioactivity left in the crude product after purge with nitrogen.
$^b$Radiochemical yield; decay-corrected, calculated from the amount of radioactivity in the crude product before nitrogen purge, and the radioactivity of the LC purified product.
$^c$Radiochemical yield; decay-corrected, calculated from analytical HPLC.

The labelled compounds were identified by HPLC retention times. Further the identity was checked with LC-MS. LC-MS chromatograms recorded at SIR M+1 m/z for each of the labelled compounds displayed peaks with the same retention time as chromatogram of corresponding reference. The reference compounds were prepared via alternative synthetic routes and characterized by NMR and MS.

This work describes convenient one-pot synthesis of 5-HT-1A subtype serotonine receptor radioligand WAY-100635 starting from [$^{11}$C]carbon monoxide, cyclohexyl iodide and amine WAY-100634. This method may become a practical alternative to Grignard synthesis.

Example 2

Experimental Setup

[$^{11}$C]Carbon dioxide production was performed using a Scanditronix MC-17 cyclotron at Uppsala IMANET. The $^{14}$N(p,α)$^{11}$C reaction was employed in a gas target containing nitrogen (Nitrogen 6.0) and 0.1% oxygen (Oxygen 4.8) which was bombarded with 17 MeV protons.

[$^{11}$C]Carbon monoxide was obtained by reduction of [$^{11}$C] carbon dioxide as described in the instant application.

The syntheses with [$^{11}$C]carbon dioxide were performed with an automated module as part of the system "Synthia 2000".

Liquid chromatographic analysis (LC) was performed with a gradient pump and a variable wavelength UV-detector in series with a β$^+$-flow detector. The following mobile phases were used: 25 mM potassium dihydrogenphosphate (A) and acetonitrile/H$_2$O: 50/7 (B). For analytical LC, a C$_{18}$, 4 μm, 250×4.6 mm ID column was used at a flow of 1.5 mL/min. For semi-preparative LC, a C$_{18}$, 4 μm, 250×10 mm (i.d.), column was used at a flow of 4 mL/min. An automated synthesis system, Synthia was used for LC injection and fraction collection.

Radioactivity was measured in an ion chamber, Veenstra Instrumenten by, VDC-202.

A Philips HOK 4/120SE mercury lamp was used as UV radiation source.

In the analysis of the $^{11}$C-labeled compounds, unlabeled reference substances were used for comparison in all the LC runs.

NMR spectra of synthesized compounds were recorded at 400 MHz for $^1$H and at 100 MHz for $^{13}$C, at 25° C. Chemical shifts were referenced to TMS via the solvent signals.

LC-MS analysis was performed using a Micromass VG Quattro with electrospray ionization. A Beckman 126 pump, a CMA 240 autosampler were used.

THF was distilled under nitrogen from sodium/benzophenone.

Example 3

Preparation of [11C]-labeled Amides

A capped vial (1 mL) was flushed with nitrogen and then was charged with an amine (15 μmol), THF (200 mL) and a base (15 μmol) was added to the solution. An organo iodide (50 μmol) was added to the solution ca. 7 min before the start of the synthesis. The resulting mixture was transferred into the micro-autoclave (270 μL), pre-charged with [$^{11}$C]carbon monoxide in He at ambient temperature. The autoclave was irradiated with a mercury lamp for 400 s. The crude reaction mixture was then transferred from the autoclave to a capped vial (1 mL) held under reduced pressure. After measurement of the radioactivity the vial was purged with nitrogen and the radioactivity was measured again. The crude product was diluted with acetonitrile (0.6 mL) and injected on the semi-preparative LC. Analytical LC and LC-MS were used to assess the identity and radiochemical purity of the collected fraction.

SPECIFIC EMBODIMENTS, CITATION OF REFERENCES

The present invention is not to be limited in scope by specific embodiments described herein. Indeed, various modifications of the inventions in addition to those described herein will become apparent to these skilled in the art from the foregoing description and accompanying figures. Such modifications are intended to fall within the scope of the appended claims.

Various publications and patent applications are cited herein, the disclosures of which are incorporated by reference in their entireties.

What is claimed is:

1. A method for labeling synthesis, comprising:
   (a) providing a UV reactor assembly comprising a high pressure reaction chamber, a UV lamp and a concave mirror, wherein the high pressure reaction chamber comprises a window facing the concave mirror, a liquid inlet and a gas inlet in a bottom surface thereof,
   (b) reacting a solution of weakly nucleophilic amine with a metal base to improve the reactivity of said weakly nucleophilic amine,
   (c) adding a solution of akyl iodides to the solution of step (b) to give a solution to be labeled,
   (d) introducing a carbon-isotope monoxide enriched gas-mixture into the reaction chamber of the UV reactor assembly via the gas inlet,
   (e) introducing at high pressure said reagent into the reaction chamber via the liquid inlet,
   (f) turning on the UV lamp and waiting for a predetermined time while the labeling synthesis occur, and
   (g) collecting the labeled amide from the reaction chamber.

2. A method of claim 1, wherein the carbon-isotope monoxide enriched gas-mixture is produced by a method comprising:
   (a) providing carbon-isotope dioxide in a suitable carrier gas,
   (b) converting carbon-isotope dioxide to carbon-isotope monoxide by introducing said gas mixture in a reactor device,
   (c) trapping carbon-isotope monoxide in a carbon monoxide trapping device, wherein carbon-isotope monoxide is trapped but not said carrier gas, and
   (d) releasing said trapped carbon-isotope monoxide from said trapping device in a well defined micro-plug, whereby a volume of carbon-isotope monoxide enriched gas-mixture is achieved.

3. A method of claim 1, wherein the carbon-isotope is $^{11}$C, $^{13}$C, or $^{14}$C.

4. A method of claim 1, wherein the carbon-isotope is $^{11}$C.

5. A method of claim 1, wherein the step of introducing the reagent is performed using a pressure that is about 80 times higher than the pressure before the introduction, in order to maintain a pseudo one-phase system.

6. A method of claim 1, wherein the step of waiting a predetermined time comprises stirring in the reaction chamber to enhance the labeling synthesis.

7. A method of claim 6, wherein the step of waiting a predetermined time further comprises adjusting the temperature of the reaction chamber so that the labeling synthesis is enhanced.

8. A method for radiocarbonylation comprising reaction of carbon-isotope monoxide with a compound of formula (I) and a compound of formula (II) which is pretreated with a metal base of formula MB:

to give a labeled amide of formula (III):

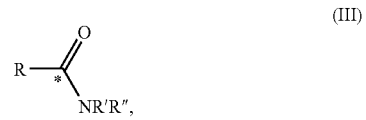

wherein R is linear or cyclic alkyl or substituted alkyl, and R' and R" are independently H, linear or cyclic alkyl, or substituted alkyl, M is Li, Na, K, Cs and Mg and B is alkyl, or diisopropylamide, hexamethyldisilylamide or YMgX, wherein Y is alky and X is a halogen.

9. A method of claim 8, wherein R may comprises chloro or fluoro groups.

10. A method of claim 8, wherein R' and R" comprise chloro or fluoro groups.

11. A method of claim 8, wherein the carbon-isotope monoxide is [$^{11}$C] monoxide.

* * * * *